United States Patent [19]
Rogers

[11] Patent Number: 5,345,081
[45] Date of Patent: Sep. 6, 1994

[54] PIT DETECTOR AND METHOD
[75] Inventor: John E. Rogers, Raleigh, N.C.
[73] Assignee: Penetect, Inc., Raleigh, N.C.
[21] Appl. No.: 942,953
[22] Filed: Sep. 10, 1992
[51] Int. Cl.[5] .................. G01N 33/02; G01N 21/35
[52] U.S. Cl. ........................ 250/338.1; 250/341.1; 250/359.1; 250/223 R
[58] Field of Search .............. 250/341, 340, 358.1, 250/359.1, 338.1, 221, 222.1, 222.2, 223 R, 224; 209/576, 577, 578; 356/52, 53, 54

[56] References Cited

U.S. PATENT DOCUMENTS

| | | |
|---|---|---|
| 3,275,136 | 9/1966 | Allen et al. |
| 3,366,236 | 1/1968 | Breazeale ............... 250/359.1 X |
| 4,146,135 | 3/1979 | Sarkar et al. ........... 209/577 X |
| 4,146,136 | 3/1979 | Ross et al. |
| 4,511,046 | 4/1985 | Walsh et al. |
| 4,666,045 | 5/1987 | Gillespie et al. |
| 4,901,861 | 2/1990 | Cicchelli |
| 4,988,875 | 1/1991 | Ortiz et al. ............ 250/341 X |
| 5,077,477 | 12/1991 | Stroman et al. |

FOREIGN PATENT DOCUMENTS 58-58466  4/1983  Japan .................. 250/359.1

OTHER PUBLICATIONS

Potential Methods for Detecting Pits in Tart Cherries E. J. Timm, P. V. Gilliland, G. K. Brown, H. A. Affeldt, Jr. Applied Engineering in Agriculture (vol. 7, No. 1, pp. 103–109, 1991).

Primary Examiner—Constantine Hannaher
Assistant Examiner—Edward J. Glick
Attorney, Agent, or Firm—Robert G. Rosenthal

[57] ABSTRACT

A method and apparatus for detecting the presence of an impurity within a substantially spherical object, such as a pit within a piece of stone fruit as it passes through an inspection zone. An infrared point source light emitting diode positioned on one side of the inspection zone transmits a single light beam across the inspection zone. A linear CCD array for generating a signal that is proportional to the intensity of the light transmitted through the fruit as the fruit passes through the inspection zone is provided and an optical slit for collimating the light beam on the CCD array are provided. An infrared filter is positioned between the lens and the CCD array. Thus, as the fruit passes through the inspection zone and is illuminated by the infrared light source and the intensity of the light transmitted through the fruit is received by the CCD array, a two-dimensional analyzable bit map representative of the cross-section of the object's density is produced.

15 Claims, 6 Drawing Sheets

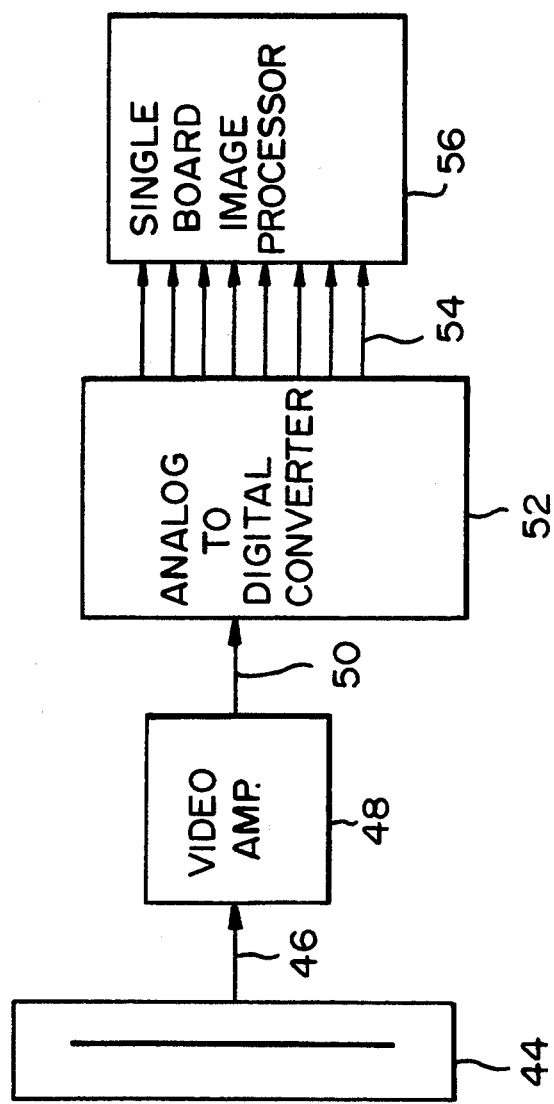

PIT DETECTOR AND METHOD

FIELD OF THE INVENTION

This invention relates generally to the field of detecting pits in fruit and more particularly to a method and apparatus for the non-destructive inspection of small fruit such as cherries and olives in order to confirm that the pit has in fact been removed therefrom.

BACKGROUND OF THE INVENTION

The problem of ensuring that pits have been removed from cherries has long been a priority for the cherry producing industry. Over 95 percent of the tart cherry crop is pitted and processed into canned, frozen and dried fruit, or made into juice. In accordance with United States Department of Agriculture procedures, pitted cherries are separated into grades. Grade A cherries may not contain more than one pit per 2.5 pounds of finished cherries. Thus, it follows that if cherries are determined to be "Grade A" the producer has a more valuable product which commands a higher price. In addition, producer liability for impure products has recently become an issue given the potential for broken teeth, etc. when served as part of a meal in a pie, topping and the like. For the foregoing reasons, the cherry producers have set a goal of not more than one pit per 62.4 pounds of finished product.

In an effort to produce a finished cherry product with fewer pits, a number of devices have been produced which inspect the cherry after it has allegedly been pitted in an attempt to ensure pit removal. U.S. Pat. No. 4,666,045 to Gillespie et al. discloses one such apparatus and a method for detecting pits in cherries. Specifically, the patent teaches an optical pit detecting device comprising an inspection zone and a scanning beam generator that sweeps a transmission scanning beam across the inspection zone. An array of sensors are positioned on the opposite side of the inspection zone and produce a series of sensor signals that are proportional to the received light intensity based on the amount of light transmitted through the cherry. A second sizing beam generator generates a signal representative of the optical path length through which the transmission scanning beam travels within the fruit and generates a signal that is proportional to the size of the fruit. The two signals are then analyzed to determine the presence or absence of a pit within the fruit.

Another method and apparatus for detecting pits in fruit was disclosed in U.S. Pat. No. 5,077,477 to Stroman et al. The device comprised a U-shaped "inspection zone" in which a first side includes a linear array of infrared light emitting diodes and an adjacent linear array of infrared light sensors. Similarly, the opposite side of the inspection zone includes an array of sensors and an adjacent array of infrared light transmitting diodes that are adapted to receive/send signal from the opposite side of the inspection zone. Also provided for each of the foregoing is means for collimating the emitted light as well as a filter for reducing the ambient and scattered light on each of the sensors. The foregoing take the form of an aperture which has a smaller diameter than the size of the corresponding sensor/emitter. The apparatus measures both the transmitted and reflected light and utilizes an algorithm based on both of the foregoing to determine the presence or absence of a pit or pit fragment. This apparatus is not preferred since the diode characteristics shift relative to each other over time which degrades performance and frequent calibration is therefore required.

The potential methods as well as what is believed to be the state of the art for detecting pits in cherries is thoroughly discussed in the article entitled "Potential Methods for Detecting Pits in Tart Cherries" by E. J. Timm et al, which appeared in the January 1991 issue of Applied Engineering in Agriculture (Vol. 7(1) at pages 103–109) published by the American Society of Agricultural Engineers, S. Joseph, Mich. 49085-9659. The reader is referred thereto for an in depth discussion of the current state of the art of detecting pits in cherries.

To date, none of the known pit detectors have been widely adopted. It is believed that this is due to a number of factors including fruit deformation, high equipment cost, unacceptable error rates, machine speeds that are uneconomical and frequent detector down time due to component failure or the necessity for cleaning.

In view of the foregoing, it is therefore an object of the present invention to provide an improved method and apparatus for the detection of pits that meets or exceeds the industry set goal of not more than one pit per 62.4 pounds of cherries.

Another object of the present invention is to provide an improved method and apparatus for the detection of pits that permits non-destructive inspection and thus does not deform the fruit.

Another object of the present invention is to provide an improved method and apparatus for the detection of pits that is reliable.

Yet another object of the present invention is to provide an improved method and apparatus for the detection of pits that inspects the product at a high rate of speed.

Still another object of the present invention is to provide an improved method and apparatus for the detection of pits that is economical.

SUMMARY OF THE INVENTION

In accordance with the present invention there is provided a method and apparatus for detecting the presence of a pit or other foreign substance present within an object as such as a stone fruit as it passes through an inspection zone. The apparatus comprises a point source light emitting means such as an infrared light emitting diode positioned on one side of the inspection zone and adapted to transmit a single light beam across the inspection zone. Means for generating a signal that is proportional to the intensity of the light transmitted through the fruit as the fruit passes through the inspection zone positioned on the opposite side of the inspection zone and additionally including means for collimating the light beam positioned between the light source and the means for generating a signal proximate the means for generating a signal.

In accordance with the method, fruit is inspected as it passes through an inspection zone. An infrared point light source is transmitted across the inspection zone through the fruit. The light beam is transmitted through the fruit and is collimated by passing it through an optical slit. The light beam is then passed through an infrared filter positioned behind the optical slit and is imaged on to a linear CCD sensor. The linear CCD sensor then produces an output signal in the form of a plurality of output voltage signals that are proportional to the intensity of the light imaged on to the linear CCD sensor at each point along its length. The output voltage signals are then converted into a digital data representative thereof. The cherry is scanned a plurality of times to generate a data set matrix and the intensity variations within the data set matrix are analyzed to determine the presence or absence of a pit.

BRIEF DESCRIPTION OF THE DRAWINGS

Additional objects and features of this invention will become apparent from the following detailed description of the invention, and from the accompanying drawings, in which

FIG. 9 is a block diagram of the circuitry employed according to the present invention that captures the bit pattern of the cherry as it traverses the inspection zone for analysis to determine the presence or absence of a pit.

DETAILED DESCRIPTION OF THE ILLUSTRATED EMBODIMENT

While the present invention will be described more fully hereinafter with reference to the accompanying drawings in which a particular embodiment is shown, it is to be understood at the outset that persons skilled in the art may modify the invention hereindescribed while still achieving the favorable results of the invention. Accordingly, the description which follows is to be understood as a broad teaching disclosure directed to persons of skill in the appropriate arts and not as limiting upon the present invention.

It will be understood at the outset that the present invention is broadly directed to an inspection station for the inspection of objects moving through an inspection zone. The invention was conceived for the inspection of stone fruit such as olives and in particular for the inspection of cherries in order to determine whether the pit has been removed therefrom. Therefore, in the specification which follows, the invention is described with particular reference to cherries, but the reader will note its utility as an inspection station in the broad sense.

Figure 1:
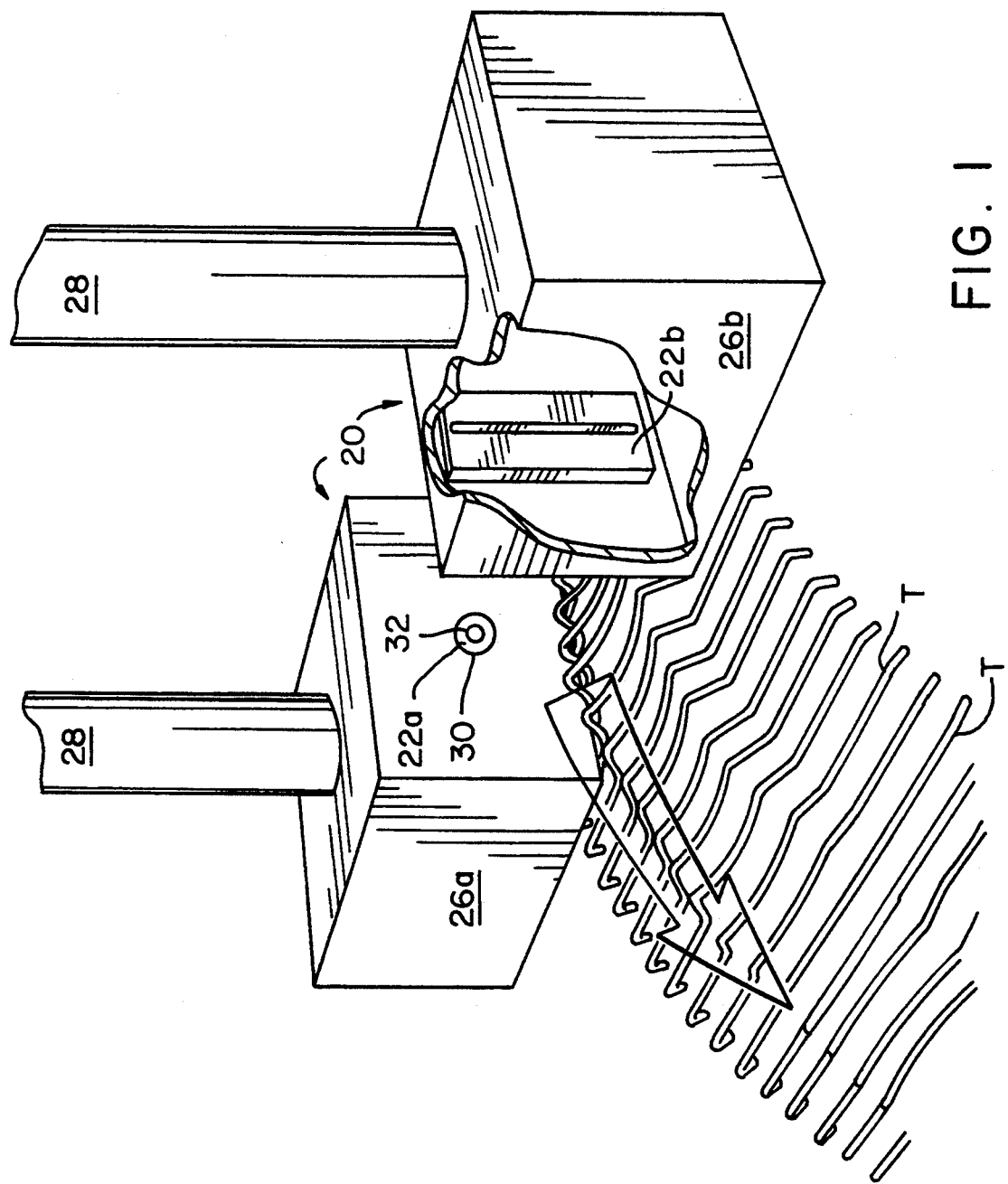
FIG. 1 is a perspective view of the pit detection apparatus according to the present invention and illustrating schematically, a stone fruit passing through the inspection zone of the detector.
Figure 2:
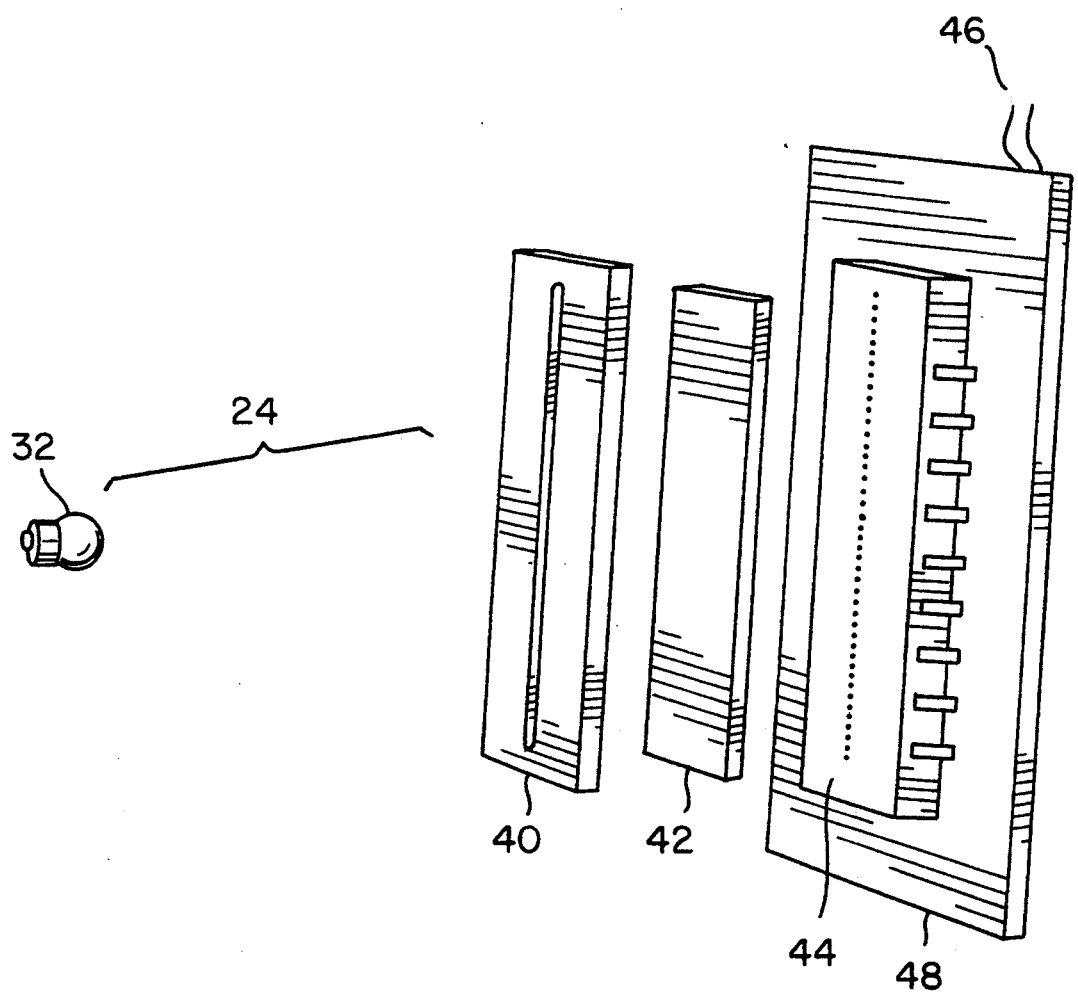
FIG. 2 is an exploded schematic view of the pit detection apparatus according to the present invention and illustrating the infrared light source on one side of the inspection zone and the detector assembly positioned on the opposite side of the inspection zone.

Referring now to the drawings and in particular to FIGS. 1 and 2, the pit detecting apparatus 20 of the present invention is there illustrated. In FIG. 1, a cherry is schematically illustrated by the arrow as moving through a sensor 22 comprising a transmitter 22a and a receiver 22b, the space therebetween defining an inspection zone 24. Also shown is a segment of a moving track T upon which the cherries rest and that moves the cherries in single file through the inspection zone. Sensors 22a and 22b are positioned within housings 26a,b which are supported from above by hollow rods 28 which are connected to a support (not shown).

Housing 26a defines a cavity and a hole defining an opening 30 which faces the inspection zone. Positioned within opening 30 is a point source light emitting means 32 which in the illustrated embodiment is an infrared light emitting diode (LED) that is adapted to transmit a single beam of light across the inspection zone. The LED also includes terminals (not shown) which are connected to a power source located remote from the LED. The point light source emitting means 32 may also be a tightly clustered optical diode array substantially emulating a point light source.

It will be noted that for the inspection of fruit, infrared light is preferred, however, the reader will note that for scanning objects of other densities, light of different frequencies may be required for effective penetration. In addition, certain objects may require light of a higher intensity than can be provided by a single diode. Therefore, the intensity can be increased by providing a number of diodes clustered together so as to emulate a point source, the significance of which will be better understood as the specification proceeds.

Housing 26b is positioned on the opposite side of the inspection zone and defines a cavity. The housing includes a means for collimating the light beam or an optical slit 40 in the form of an elongate slit in the wall of housing 26b positioned directly across the inspection zone from the light source 32. Within housing 26b behind optical slit 40 is an infrared filter 42. Located behind the infrared filter 42 and in linear alignment with both optical slit 40 and filter 42 is a means 44 for generating a signal that is proportional to the intensity of the light transmitted through the cherry. In the preferred embodiment the means for generating a proportional signal 44 takes the form of a linear photosensitive receiver such as a linear CCD device as is commonly found in facsimile or "fax" machines or photodiode array. One such device is the TCD 133 manufactured by Toshiba which produces a 2048×1 bit output signal in the form of a serial voltage signal on line 46. The circuitry required to drive CCD sensor 44 is well known to persons skilled in the art and a detailed discussion is not deemed necessary. Therefore, it is shown schematically as being attached to circuit board 48.

Figure 3:
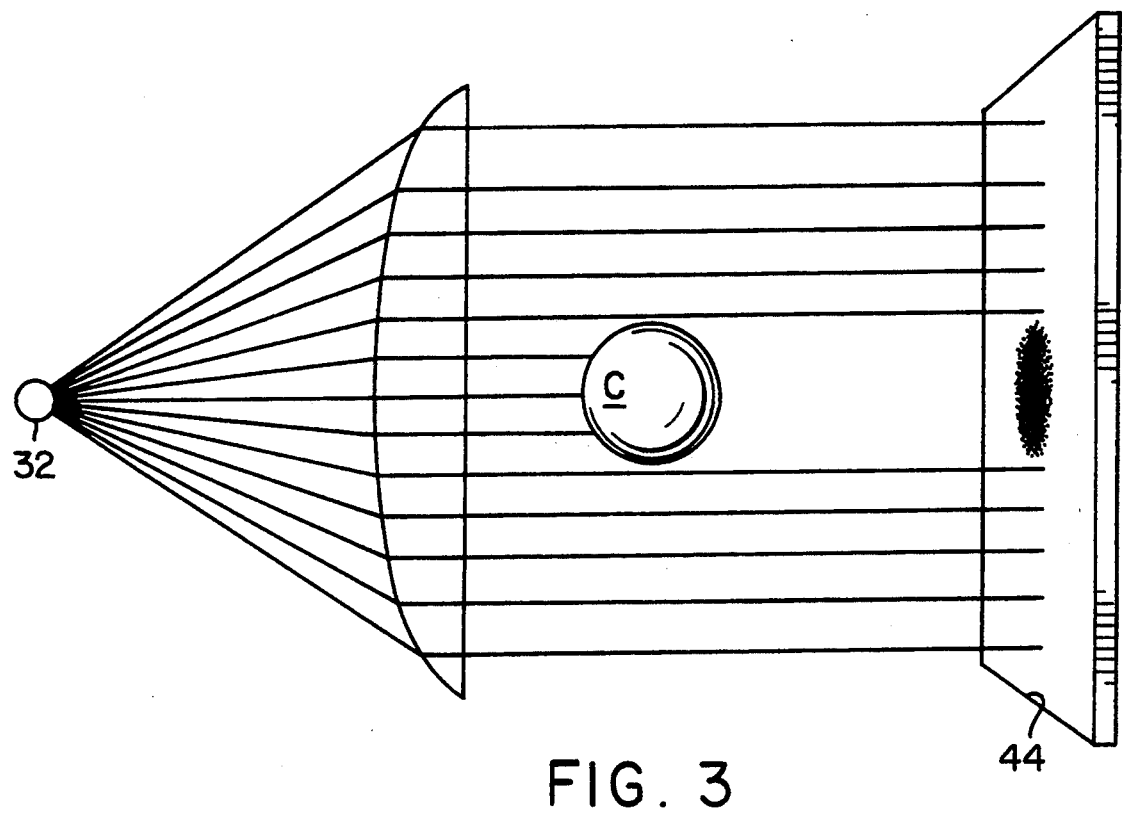
FIG. 3 is a schematic view of the desired collimation of the light source as it passes through a cherry so that a clear image of the cherry is projected on to a focal plane for analysis.
Figure 4:
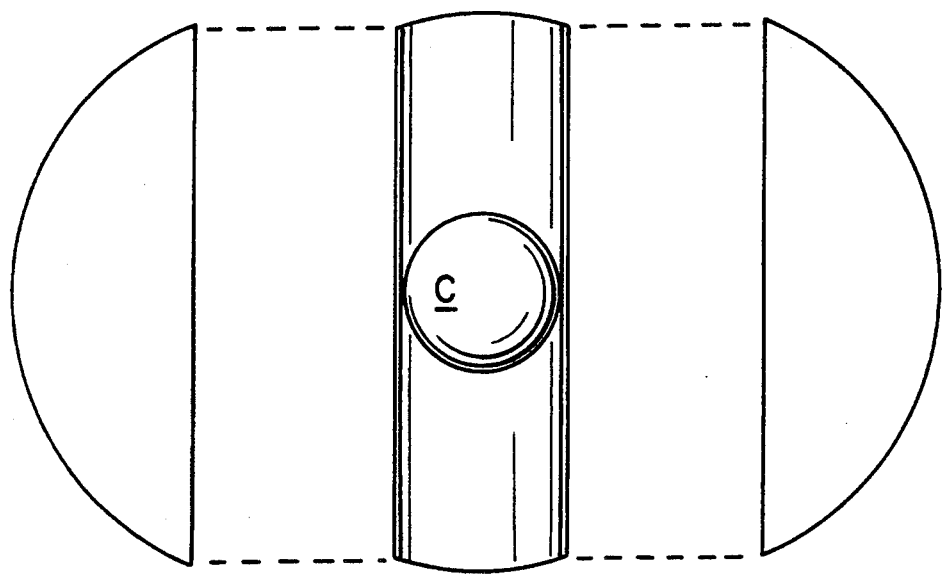
FIG. 4 is a schematic view of a cherry as a convex lens on one side and a concave lens on the opposite side.
Figure 5:
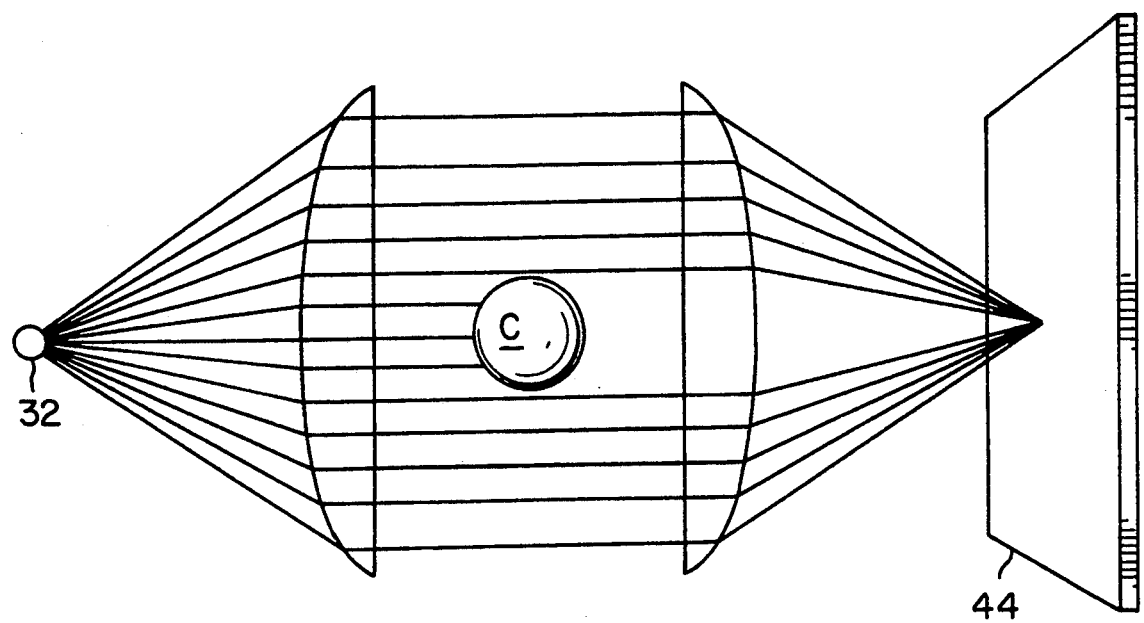
FIG. 5 is a schematic view of a beam of light emanating from a point source passing through the front half of a cherry and becoming collimated and then passing through the back half of the cherry and being converged by the lens action.
Figure 7:
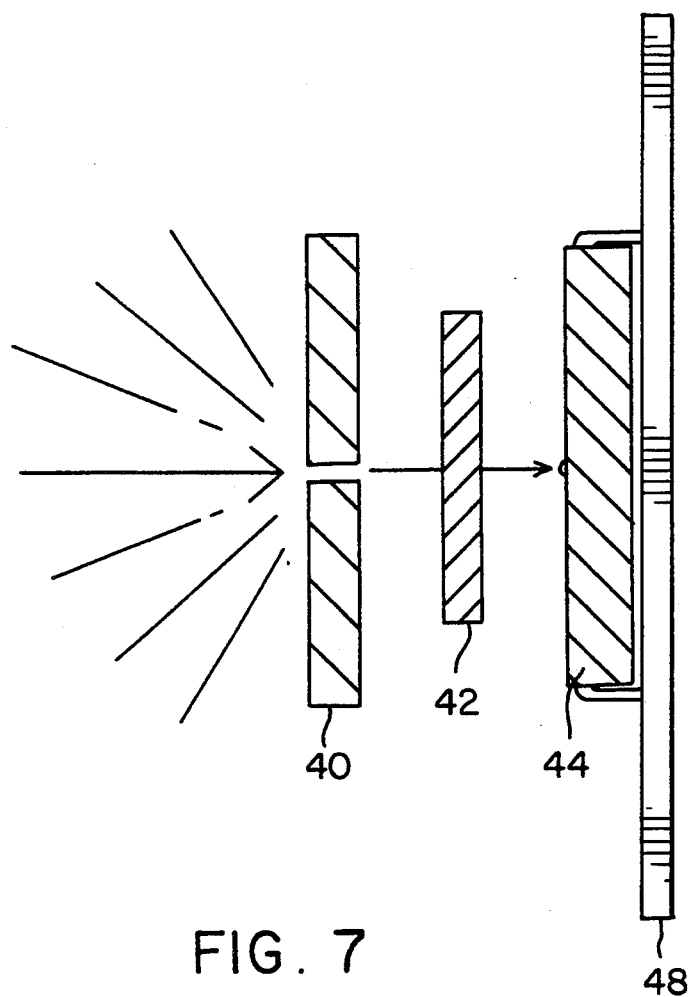
FIG. 7 is a schematic top plan view of how the optical slit in the present invention acts to collimate the beam so that an image is provided on the focal plane as the stone fruit traverses the inspection zone.

The input section of the pit detector having just been described, it will be helpful to the reader to understand the theory of operation of the apparatus which is illustrated in FIGS. 3 through 6. Referring now to FIG. 3, a cherry C is depicted as being in the optical path of light source 32 in order to accurately detect the presence/absence of a pit, a shadow as illustrated on focal plane 44 must be created. In the ideal case, a collimating lens that would collimate the beam emanating from the point light source would be positioned in front of the cherry. A collimated beam is precisely what is required in order to image the cherry pit clearly onto focal plane 44 in order to capture the transmitted light for analysis of the relative intensities thereof. The density variations that occur directly correlate with the presence or absence of a pit or other foreign substance. However, as the cherry is substantially spherical, the front half acts to collimate the light and the second or back half thereof acts to bend the light back towards a point source, thus collapsing the image prior to its reaching the focal plane 44 as shown in FIGS. 4 and 5. This phenomenon is illustrated in FIG. 4 wherein the cherry C is shown as a sphere and schematically as a pair of lenses on each side of a central slice having parallel sides (substantially without light bending qualities). The effect of the lens system that is described in FIG. 4 is illustrated in FIG. 5. The IR light emanates from the IR point source 32, passes through the front portion of the cherry which collimates the beam. But as the light passes through the back half of the cherry, the light is bent back towards a point which collapses the image back to a point source on to focal plane 44.

Figure 6:
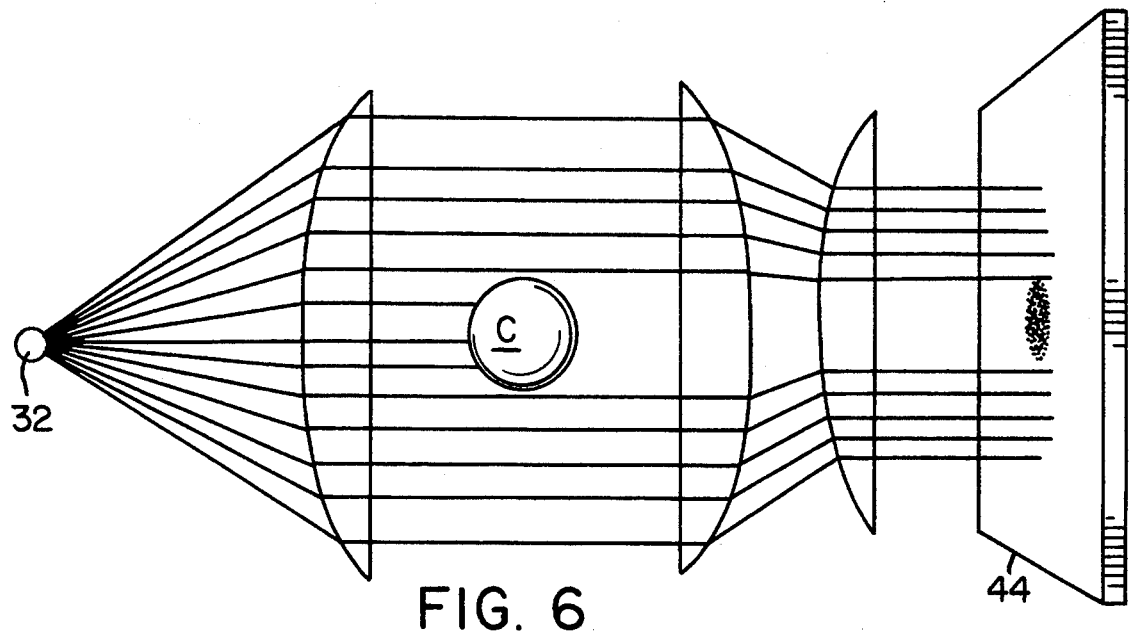
FIG. 6 is a schematic view of a beam of light emanating from a point source passing through the front half of a cherry and becoming collimated and then passing through the back half of the cherry and converging and further illustrating a corrective lens that would have to be employed in order to recollimate the beam so that it focuses on the focal plane.

Thus, it will be seen that in order to produce a system that images a cherry on to a remote focal plane must not allow the transmitted light to converge as theoretically illustrated in FIG. 6. Specifically, FIG. 6 illustrates schematically the present system which prevents convergence of the transmitted light. As previously mentioned, the cherry acts to collimate and then refract the light beam back towards a point source as it passes through the cherry. A mechanism must therefore be provided which cancels the tendency of the back half of the cherry to refract the light beam back to a point source on the focal plane 44. This mechanism is schematically illustrated in FIG. 6 by the lens adjacent the focal plane 44 and in the illustrated embodiment comprises an optical slit in the form of an elongate slit. Those knowledgeable in the art of optics will recognize that the optical slit operates on essentially the same principals as the "pin-hole" camera. As the cherry moves through the field of view only rays perpendicular to the focal plane are permitted to pass through the optical slit to illuminate the sensor. This action dynamically simulates recollimation of the image as illustrated in FIG. 6. The deep depth of field provided by the optical slit essentially eliminates the need for any type of active focusing system which would have been required to compensate for variations in cherry size and shape.

Figure 8:
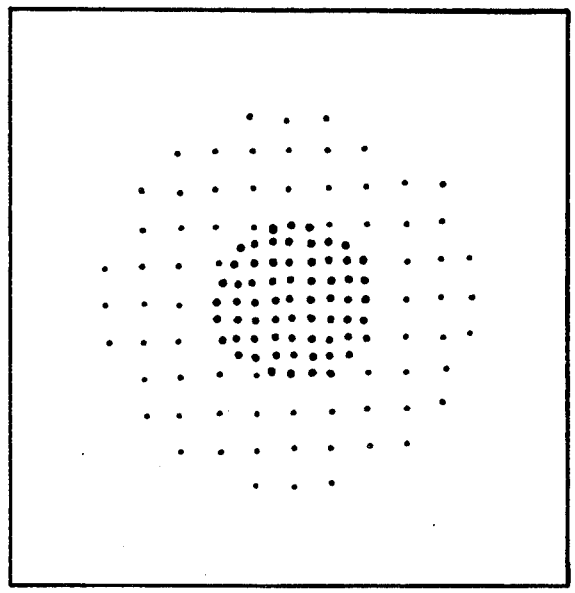
FIG. 8 is a front view of the focal plane according to the present invention and illustrating the bit pattern representative of a cherry containing a pit that is created for analysis after the cherry has traversed the inspection zone.

In operation, the cherry is moved via track T between the infrared light source 32 positioned in housing 26a and the receiving sensor 22b positioned in housing 26b. As the cherry is moved through the inspection zone, the light beam from the infrared diode 32 penetrates the cherry and the CCD 44 is pulsed every 4 milliseconds so as to obtain a plurality of vertical "slices" of the cherry which are output on line 46 and each of which contains 2048 separate elements representative of the intensity of light transmitted through the cherry. Thus, the intensity of the received light when a pit is present will be lower then when passing only through the fruit. This series of output voltages on line 46 is then input to a video amplifier 48 in order to amplify the signal to a level where it can be input into analog to digital converter 52 which produces an 8 bit output signal on line 54 which is then input to a computing means 56 such as a single board image processor and is stored in a buffer therein (not illustrated). The stored image is similar to that illustrated in FIG. 8 where the darker data points represent higher output voltages from the analog to digital converter and represent the portion of the cherry containing the higher density pit. The digital data is then analyzed by the image processing means or image processor 56 in order to determine the presence or absence of a pit. The algorithms are not discussed here as they are well known to those skilled in the art. Furthermore, as the quality of the stored data representative of the relative density across the cherry improves, the accuracy of detection improves proportionately.

The foregoing embodiments and examples are to be considered illustrative, rather than restrictive of the invention, and those modifications which come within the meaning and range of equivalence of the claims are to be included therein.

That which is claimed is:

1. An apparatus for detecting the presence of a pit within a stone fruit passing through an inspection zone and comprising:
   a) a point source light emitting means positioned on one side of the inspection zone and adapted to transmit a single light beam from one side of the inspection zone across the inspection zone to the opposite side of the inspection zone;
   b) means for generating a signal that is proportional to the intensity of the light transmitted through the fruit as the fruit passes through the inspection zone positioned on the opposite side of the inspection zone; and
   c) means for collimating said light beam positioned on the opposite side of said inspection zone, proximate said means for generating a signal;
   whereby as the fruit passes through the inspection zone and is illuminated by the light source and the intensity of the light transmitted through the fruit is received by the means for generating a signal, a two dimensional analyzable bit map representative of the cross-sectional density is produced.

2. The pit detecting apparatus according to claim 1 wherein said point source light emitting means comprises an infrared diode and further including an infrared filter positioned between said means for collimating the light beam and said means for generating a signal that is proportional to the intensity of the transmitted light.

3. The pit detecting apparatus according to claim 1 wherein said means for generating a signal that is proportional to the intensity of the light that is transmitted through the fruit comprises a linear CCD array.

4. The pit detecting apparatus according to claim 1 wherein said means for collimating the light beam comprises an optical slit and further wherein said means for generating a signal that is proportional to the intensity of the light transmitted through the fruit comprises a linear CCD array in alignment with said optical slit.

5. The pit detecting apparatus according to claim 1 further including means for digitizing the signal that is proportional to the intensity of the light transmitted through the fruit.

6. The pit detecting apparatus according to claim 5 further including means for creating a bit map representative of the relative intensities of the light transmitted through the fruit.

7. The pit detecting apparatus according to claim 6 further including image processing means for analyzing said bit map in order to detect the presence of a pit.

8. The pit detecting apparatus according to claim 1 wherein said means for generating a signal that is proportional to the intensity of the light that is transmitted through the fruit comprises a photodiode array.

9. An apparatus for detecting the presence of a foreign substance within a substantially spherical object passing through an inspection zone and comprising:
   a) an infrared point source light emitting means positioned on one side of the inspection zone and adapted to transmit a single light beam across the inspection zone to the opposite side of the inspection zone;
   b) a linear CCD array for generating a signal that is proportional to the intensity of the light transmitted through the object as the object passes through the inspection zone positioned on the opposite side of the inspection zone;
   c) an optical slit for collimating the light beam onto the linear CCD array in alignment therewith, said optical slit being positioned on the opposite side of the inspection zone proximate said linear CCD array between the linear CCD array and the infrared point source light emitting means;
   d) an infrared filter in alignment with and between said optical slit and said linear CCD array;
   whereby as the object passes through the inspection zone and is illuminated by the infrared light source and the intensity of the light transmitted through the object is received by the linear CCD array, a two dimensional analyzable bit map representative of the cross-section of the object's density is produced.

10. A method of inspecting a stone fruit passing through an inspection zone comprising the steps of:
    a) transmitting an infrared point source light beam from one side of the inspection zone across the inspection zone to the opposite side of the inspection zone;
    b) collimating the light beam by passing it through an optical slit positioned on the opposite side of the inspection zone;
    c) filtering the light beam by passing it though an infrared filter positioned behind the optical slit;
    d) imaging the light beam on to a linear CCD sensor positioned behind the filter;
    e) producing an output signal in the form of a plurality of output voltage signals that are proportional to the intensity of the light imaged on the linear CCD sensor at each point along its length.

11. The method according to claim 10 further including the step of converting the plurality of output voltage signals into a digital data set representative thereof.

12. The method according to claim 11 further including the step of analyzing the digital data set, whereby the presence or absence of a pit based on variation of transmitted light intensity through the stone fruit is determined.

13. A method of inspecting a substantially spherical object passing through an inspection zone for the presence of a foreign substance comprising the steps of:
    (a) transmitting a point source light beam from one side of the inspection zone across the inspection zone to the opposite side of the inspection zone;
    (b) collimating the light by passing it through an optical slit positioned on the opposite side of the inspection zone;
    (c) imaging the light beam on to a linear photosensitive receiver positioned behind the optical slit;
    (d) producing an output signal from the linear photosensitive receiver in the form of a plurality of output voltage signals that are proportional to the intensity of the light imaged on to the linear photosensitive receiver at each point along its length.

14. The method according to claim 13 further including the step of converting the plurality of output voltage signals into a digital data set representative thereof.

15. The method according to claim 14 further including the step of analyzing the digital data set, whereby the presence or absence of an impurity based on the variation of transmitted light intensity through the object may be determined.

* * * * *